United States Patent
Bouras

(10) Patent No.: US 9,572,826 B2
(45) Date of Patent: Feb. 21, 2017

(54) COMPOSITIONS FOR THE TREATMENT OF HAIR LOSS

(76) Inventor: Elias Bouras, Bognor Regis (GB)

( * ) Notice: Subject to any disclaimer, the term of this patent is extended or adjusted under 35 U.S.C. 154(b) by 534 days.

(21) Appl. No.: 12/996,899

(22) PCT Filed: Jun. 17, 2009

(86) PCT No.: PCT/GB2009/050687
§ 371 (c)(1),
(2), (4) Date: Dec. 8, 2010

(87) PCT Pub. No.: WO2010/004303
PCT Pub. Date: Jan. 14, 2010

(65) Prior Publication Data
US 2011/0076328 A1 Mar. 31, 2011

(30) Foreign Application Priority Data
Jun. 17, 2008 (GB) .................................. 0811053.8

(51) Int. Cl.
*A61Q 7/00* (2006.01)
*A61K 31/704* (2006.01)
*A61K 31/7048* (2006.01)

(52) U.S. Cl.
CPC ......... *A61K 31/704* (2013.01); *A61K 31/7048* (2013.01)

(58) Field of Classification Search
None
See application file for complete search history.

(56) References Cited

U.S. PATENT DOCUMENTS

| 4,147,768 | A | * | 4/1979 | Shaffer et al. | 424/466 |
| 5,026,691 | A | * | 6/1991 | Kligman | 514/171 |
| 6,030,948 | A | * | 2/2000 | Mann | 514/9.7 |
| 2005/0026849 | A1 | * | 2/2005 | Singh et al. | 514/26 |

FOREIGN PATENT DOCUMENTS

KR   908745   *   7/2009

OTHER PUBLICATIONS

"Permeation enhancers" in Drug devlopent and industrial Pharmacy, vol. 26, pp. 1131-1140 (2000).*
Olsen et al., "Evaluation and treatment of male and female pattern hair loss", Journal of the American Academy of Dermatology, C.V. Mosby, St. Louis, MO, vol. 52, No. 2, Feb. 1, 2005, pp. 301-333.
Pursley T V et al., "Tinea capitis in the elderly", International Journal of Dermatology, 1980, vol. 19, No. 4, p. 220, Database Embase [Online] Elsevier Science Publishers, Amsterdam, NL.

* cited by examiner

*Primary Examiner* — Jyothsna Venkat
(74) *Attorney, Agent, or Firm* — David Guerra

(57) ABSTRACT

A composition for the treatment or prevention of a disorder resulting in hair loss comprises a cardiac glycoside as active principal.

23 Claims, No Drawings

COMPOSITIONS FOR THE TREATMENT OF HAIR LOSS

CROSS-REFERENCE TO RELATED APPLICATIONS

This application is an U.S. national phase application under 35 U.S.C. §371 based upon co-pending International Application No. PCT/GB2009/050687 filed on Jun. 17, 2009. Additionally, this U.S. national phase application claims the benefit of priority of co-pending International Application No. PCT/GB2009/050687 filed on Jun. 17, 2009, and Great Britain Application No. 0811053.8 filed on Jun. 17, 2008. The entire disclosures of the prior applications are incorporated herein by reference. The international application was published on Jan. 14, 2010 under Publication No. WO 2010/004303.

BACKGROUND OF THE INVENTION

Field of the Invention

The present invention relates to compositions which comprise a cardiac glycoside or cardiac glycosides for use in the treatment and prevention of hair loss conditions and disorders.

Description of the Prior Art

Hair loss is an extremely prevalent condition and it is estimated that approximately 20 to 25% of the population suffer from some type of hair loss disorder. Whilst hair loss is more common in adult males, hair loss disorders also affect women and children. Although most hair loss disorders are not in themselves damaging to the health of an individual, many sufferers report associated psychological problems including anxiety and depression.

However, despite the prevalence of hair loss disorders, few efficacious treatments are available. Surgical treatments are available for the restoration of hair, particularly to the scalp. However, these techniques are painful, expensive, and suffer from the inherent dangers associated with any invasive surgery. Furthermore, hair restoration surgeries typically require at least some areas of dense hair growth to be available on the patient for transplant or relocation to other areas of the body. Yet further, surgical treatments are rarely applicable to sufferers of alopecia areata in which spontaneous regrowth of hair which subsequently falls out again, often occurs.

Hair loss compositions are thus an attractive proposition for those suffering from hair loss conditions. A range of therapies are available for which partial success in the treatment of alopecia has been claimed. The various therapies available can be divided up into several groups comprising non-specific immunosuppressants such as corticosteroids or UVA treatment, contact dermatitis inducers, specific immunosuppressants such as cyclosporins, non-specific irritants and other treatments such as alternative and experimental therapies.

Non specific immunosuppressants such as corticosteroids function by mimicking the steroidal hormones produced by the adrenal glands to suppress inflammation. Corticosteroids can be administered topically to the affected area, through intralesional injections, or systemically via injection or oral medication, depending on the severity of the condition. While topical corticosteroids are commonly used to treat alopecia areata, there is little evidence that they promote hair regrowth. Intralesional administration of corticosteroids has demonstrated more efficacy in the treatment of alopecia areata, with a study reported by Porter and Burton (Br. J. Dermatol. 1971:85, 272-273) demonstrating that hair regrowth was achieved in 33 out of 34 sites injected with triamcinolone hexacetonide in 11 patients and in 16 out of 25 sites injected with triamcinolone acetonide in 17 patients, with the affects lasting about nine months. However, intralesional corticosteroid administration is most suitable for treating patchy hair loss of limited extent and for cosmetically sensitive sites such as the eyebrows, with skin atrophy at the site of injection a consistent side-effect. Systemic corticosteroid administration has achieved some hair regrowth in alopecia suffers. However, studies have demonstrated only 30-47% of patients showed significant hair regrowth and thus in most patients the response achieved is insufficient to justify the risks associated with prolonged treatment.

A combination of UVA actinotherapy with 8-methoxypsoralen (an irritant and immuno-modulator) has also been utilised for the treatment of alopecia. However, this method of treatment, commonly called PUVA, is not popular due to the frequency of treatment required, potentially dangerous side-effects and low success rates. Furthermore, the relapse rate following treatment is high and continued treatment is usually required which may lead to high cumulative UVA dosages.

Contact dermatitis inducers work by sensitising the immune system. A low level of the drug is initially applied and adjusted until a reaction is established. Contact dermatitis inducers utilised for the treatment of alopecia areata include dinitrochlorobenzene (DNCB), diphenylcyclopropenone (DPCP) and squaric-acid-dibutylester (SADBE). Reviews of these treatments have concluded that the range of response rates is wide, at reportedly 9 to 87% (Rokhsar et al. J Am Acad Dermatol 1998:39:751-761). Side affects including severe dermatitis and occipital and/or cervical lymphadenopathy are often common.

Specific immunosuppressants for the treatment of alopecia include cyclosporins and tacrolimus (FK506). These drugs act by inhibiting T-cell activation. While results have demonstrated some efficacy for cyclosporins, side-effects are a major consideration and results may often not justify the associated risks.

Non-specific irritants function by interrupting cell differentiation in the skin with the damage caused stimulating immune cell activity. Irritants that have been employed for the treatment of alopecia areata include anthralin, iodine, chrysarobin, croton oil, capsicum and dithranol. However, results in studies on anthralin indicate low levels of efficacy with one open study demonstrating significant regrowth in just 18% of patients. Furthermore, staining of hair limits the use of anthralin in fair-haired patients.

Alternative treatments such as essential oils and acupuncture and experimental and theoretical treatments such as cytokines, biologicals, desensitisation, oral tolerance and gene therapy have been variously employed in the treatment of alopecia with varying degrees of success.

Recent research has indicated that a technique called follicular cell implantation, in which dermal papilla cells are taken from the patient, multiplied in a laboratory and then injected into the affected area, may be effective in the treatment of hair loss disorders with 11 out of 19 patients reporting hair regrowth. However, this technique is at an early stage of development and results thus far are based on a very small number of patients, making the efficacy of this treatment difficult to assess.

All hair loss treatments currently known require long-term regular use to maintain any efficacious effects achieved. Of the above treatments, many require administration by a health care professional and involve potentially dangerous side-effects. Currently few hair loss compositions which can be self-administered have demonstrated clinical efficacy in the treatment or prevention of hair loss. Minoxidil, or 3-hydroxy-2-imino-6-(1-piperidyl)pyrimidin-4-amine is a vasodilatory medication that was discovered to have the side-effect of promoting hair growth when used to treat high blood pressure. The mechanism by which minoxidil promotes hair growth is not well understood, although it has been postulated that it may be due to an increase in blood supply to the hair follicles. Whilst minoxidil has demonstrated some efficacy in promoting hair growth, it is considered to be effective in less than 60% of patients, with there currently being no indication as to which patients are most likely to respond.

Finasteride has also demonstrated some efficacy in treating hair loss. Finasteride is a 5α-reductase inhibitor, which functions by blocking the conversion of testosterone to the active 5α-dihydrotesterone (DHT) form, elevated levels of which have been linked to hair loss. Studies indicate effectiveness in approximately 50% of patients, with side effects including erectile dysfunction and gynecomastica being reported. Furthermore finasteride is not indicated for use in women of childbearing age as it can cause birth defects in unborn babies.

Oxalates have also been reported to demonstrate efficacy in the treatment of hair loss disorders. International Patent Application No. WO 94/15574 discloses that oxalates of group Ia or IIa metals could be used for preventing hair loss and stimulating growth and Canadian patent No. 888689 discloses the use of a composition for the treatment of the scalp against hair loss which requires the use of an emulsion containing bergamot oil, water and a ferrous salt including a ferrous oxalate (i.e. a group VIII metal salt). However, oxalates such as calcium oxalate as described in the prior art appear as crystals which can pierce and intensely irritate the skin, making oxalates unsuitable for some patients.

SUMMARY OF THE INVENTION

Therefore, despite active research in this area and a large number of proposed active ingredients there remains the need for a hair loss composition which demonstrates efficacy in a wide populace with minimal side effects. Furthermore, for each of the above described compositions, prolonged treatment is required with results typically demonstrated after approximately four months of continuous treatment. Thereafter, maintenance of any beneficial effect obtained is dependent upon continued use of the compositions, with any hair growth that has been achieved often falling out upon cessation of treatment. These hair loss compositions therefore require ongoing use, representing an expensive means of treatment. In addition, all of the current modalities used are more effective in those presenting with milder forms of the condition, but much less effective in patients already suffering from extensive hair loss. In summary, therefore, known hair loss compositions are expensive, have limited efficacy and exhibit potentially damaging side-effects. Consequently the search for effective compositions for treatment and prevention of hair loss disorders is ongoing.

The applicant has now discovered that cardiac glycosides are a highly effective active ingredient in compositions for the treatment and prevention of hair loss.

Accordingly, the first aspect of the present invention provides a composition comprising a cardiac glycoside as active principal for use in the treatment or prevention of a condition or disorder resulting in hair loss.

DESCRIPTION OF THE PREFERRED EMBODIMENT

The composition preferably comprises an effective amount of cardiac glycoside for the treatment of prevention of a hair loss condition. The cardiac glycoside may be isolated from a natural source and is preferably purified before inclusion in the composition in order that the composition comprises a cardiac glycoside in substantially pure form.

Disorders and conditions which can result in hair loss include hereditary and congenital alopecia, hypotrichosis, trichotillomania, tinea capitis, telogen effluvium, anagen effluvium, monilethrix, trichorrhexis nodosa (trichonodosis), infections which involve the hair or scalp such as mycotic infection, infestations involving the hair or scalp, endocrine conditions such as hyperthyroidism, hypothyroidism and diabetes mellitus, lupus, hormone imbalance, for example as a result of polycystic ovary syndrome, and sebaceous cysts.

Preferably, the composition is for use in the treatment or prevention of alopecia or hypotrichosis, and more preferably in the treatment of alopecia areata.

The term "alopecia" as used herein is taken to mean a disease in which the hair falls out and includes, but is not limited to alopecia areata, male and female pattern baldness, alopecia androgenetica, alopecia totalis, alopecia universalis, alopecia partialis, alopecia barbae, alopecia cicatricial, alopecia areata ophiasis, alopecia areata diffusa, reticular alopecia areata, sisaipho alopecia areata, congenital alopecia, drug-induced alopecia, alopecia mucinosa, alopecia marginalis, androgenetic alopecia, traction alopecia and syphilitic alopecia.

Alopecia areata is a non-scarring inflammatory hair loss disease that manifests itself in many forms, resulting typically in patchy areas of hair loss and thinning of the hair. Alopecia areata typically results in smooth, round or oval bald areas. As the disease progresses, the first one or two patches may expand in size and/or other patches of hair loss may subsequently develop. Alopecia areata most frequently occurs on the scalp, but any hair-bearing region of skin on the body can be affected. The pathophysiology of alopecia areata remains unknown, although the most widely accepted hypothesis is that alopecia areata is a T-cell mediated autoimmune condition that is likely to occur in genetically predisposed individuals. An unknown environmental trigger such as emotional stress, physical trauma or a pathogen is thought to combine with hereditary factors to cause the condition. Alopecia areata may spontaneously regress, become chronic, or spread diffusely. Risk factors for chronicity include extensive involvement, onset before adolescence, atopy and involvement of the peripheral scalp (ophiasis). Presently there is no permanent cure for alopecia areata and there is no clinically proven therapy for inducing remission. Research thus far cannot explain disease exacerbation and the trigger mechanism in most patients. Potentially everyone with alopecia areata is capable of regrowing hair even after many years of hair loss and spontaneous regrowth can occur. However, this regrowth may not be permanent.

Specifically, the composition may be used in the treatment or prevention of alopecia areata associated with X-linked dominant disorders, autosomal dominant or autosomal recessive disorders.

Cardiac glycosides are a group of glycosides which have an inotropic effect on the heart muscle, which are characterised by an aglycone consisting of a steroid nucleus with a α, β-unsaturated lactone ring attached at the C-17 position. More than 200 naturally occurring cardiac glycosides have been identified. While cardiac glycosides are usually obtained from plant sources such as the foxglove (*Digitalis puourea*) or lily of the valley (*Convallaria majalis*), they are also present in large quantities in the venom gland of cane toad (*Bufo marinas*).

Cardiac glycosides are divided into two main types, characterised by the lactone ring at the C-17 position. Bufadienolides are C24 compounds, containing a doubly unsaturated six-membered lactone ring (α-pyrone), whilst cardenolides are C23 compounds comprising an unsaturated butyrolactone ring. Figure 1 illustrates the structure of a typical bufadienolide and a cardenolide.

FIG. 1-main classes of cardenolide: (a) bufadienolide and (b) cardenolide.

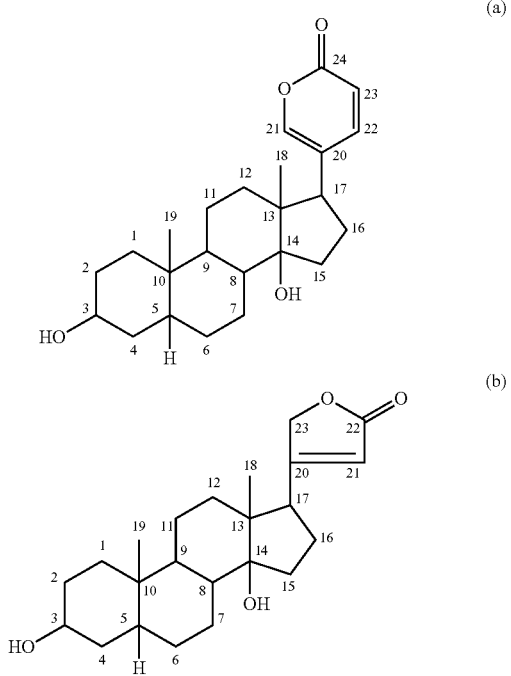

Cardiac glycosides function as inotropic agents by influencing the contractility of muscular tissue and are used medicinally primarily to increase the force of contraction of the heart muscle and regulate heartbeat. Their mechanism of action is well established and involves inhibition of the plasma membrane $Na^+/K^+$-ATPase, leading to alterations in intercellular $K^+$ and $Ca^{2+}$ levels.

In medical practice *digitalis* glycosides are administered at doses that produce a moderate degree of enzyme inhibition, roughly 30%, in cardiac muscle. When the muscle cell membrane is depolarized by the action of cardiac glycosides, there are fewer uninhibited $Na^+/K^+$-ATPase enzymes available for the restoration of the $Na^+/K^+$ balance after muscle contraction. The remaining $Na^+/K^+$-ATPase enzymes which are not inhibited by cardiac glycosides will increase their rate of ion transport due to the high $[Na^+]i$. For the muscle cell to respond correctly the next triggering nerve impulse, the $Na^+/K^+$ ionic gradient must be restored, although restoration of the gradient will take longer than it would if every $Na^+/K^+$-ATPase were available.

This lag causes a temporary increase of $[Na^+]i$. This temporary increase of $[Na^+]i$ causes $Ca^{2+}$ to move into the cell through a $Na^+/Ca^{2+}$ ion channel. The $Na^+/Ca^{2+}$ ion channel allows $Na^+$ to exit from the cell in exchange for $Ca^{2+}$, or $Ca^{2+}$ exit from the cell in exchange for $Na^+$, depending on the prevailing $Na^+$ and $Ca^{2+}$ electrochemical gradients (Blaustein 1974). In this way inhibition of the $Na^+/K^+$-ATPase by cardiac glycosides causes the $Na^+/Ca^{2+}$ exchange to partly reverse resulting in increased intracellular $Ca^{2+}$, which in turn causes increased muscle contractility.

When the concentration of *digitalis* glycosides reaches toxic levels, enzyme inhibition approaches 60% thus decreasing $Na^+$ and $K^+$ transport to the extent that the restoration of normal ion transmembrane gradient during diastole is not possible before the next depolarization and contraction cycle. Then, a sustained increase of $[Na^+]i$, and thus of $[Ca^{2+}]i$, gives rise to the cardiotoxic effect, i.e. arrhythmia, of these molecules.

*Digitalis* glycosides represent a very important group of drugs for the treatment of heart failure but have the disadvantage of a narrow therapeutic index, so they must be administered under a strict supervision with continuous monitoring of plasma drug levels. $Na^+/K^+$-ATPase inhibition at therapeutic doses is the mechanism of their positive inotropic effect, since only small changes in $[Na^+]i$ result in a large change of contractile force (Lee 1985).

The term "cardiac glycoside" as used herein is taken to encompass both naturally-occurring cardiac glycosides as well as their analogues. Cardiac glycosides for use in the composition of the invention may be extracted and purified from natural sources such as *digitalis puipurea* in accordance with US pharmacopoeia standards or may be synthesized by known methods, for example as described by Simbi and van Heerden (*J. Chem. Soc., Perkin Trans.* 1, 1997). Preferably, the cardiac glycosides are comprised in the composition in a substantially pure form. Preferably, the cardiac glycosides are at least 95% pure by weight, preferably at least 96% pure by weight, preferably at least 97% pure by weight, preferably at least 98% pure by weight, and preferably at least 99% pure by weight.

Suitable cardiac glycosides for use in the compositions of the invention include but are not limited to digitoxin, digoxin, digitonin, proscillaridin-A, proscillaridin-B, methyl-proscillaridin-A, oleandrin, odoroside-A, odoroside-H, neriifolin and ouabain.

Preferably, the cardiac glycoside is derived from a plant extract. When extracted from a natural source, it is preferred that the cardiac glycoside is substantially free of mucilage, as crude extracts from plant products make the exact amount of active ingredient present in the extract difficult to assess. Furthermore, crude extracts from plant sources require larger volumes of inactive composition ingredients, resulting in increased production costs.

Preferred cardiac glycosides are those derived from the *digitalis* (foxglove) genus, namely digitoxin, digoxin and digitonin. Digipuratum, which is a standardized extract of uniform strength, may also be employed.

Preferably, the composition is substantially free of oxalates. Oxalates, which may be present in plant matter from which the cardiac glycosides are extracted, can pierce and intensely aggravate and irritate the skin thus making them undesirable components of the composition.

Alternatively, the cardiac glycoside may be synthetic. Synthetic cardiac glycosides may be synthesized by any suitable route.

The cardiac glycoside may be the only active ingredient present in the composition. The active principal is preferably in a semi-solid or semi-liquid form containing one or more active compounds. Generally the active principal is included in a lotion or ointment at 0.001 mg/g to 25 mg/g by weight but preferably in the order of 0.04 mg/g to 2 mg/g by weight. However, the amount of active ingredient may be varied according to the individual objective, i.e. whether to prevent initial or further hair loss or whether to stimulate regrowth.

Optionally, the cardiac glycoside may be adjunctively administered with at least one active ingredient, i.e. the composition may further comprise adjuvant compounds which exhibit efficacy in treating hair loss disorders or symptoms associated therewith. Preferably, the composition may comprise at least one component selected from the group consisting of a steroid, an indole-based compound, an anti-fungal agent, an anti-inflammatory agent and a cooling or antipruritic agent.

It has been reported that reduced production of androgens, estrogens and epidermal growth factor (EDG) can be useful in the treatment and prevention of hair loss. Accordingly, steroids which block or inhibit a hormone or factor associated with hair loss can optionally be added to the composition. As an example, 5α-reductase inhibitors block the conversion of testosterone to the active 5α-dihydrotesterone (DHT) form and have been used in the treatment of hair loss disorders. Suitable steroids for the reduced production and inhibition of these compounds and factors include testolactone, pregnenolone, dehydroepiandrosterone (DHEA) diosgenin, spironolactone, finasteride and tamoxifen.

Indole-based compounds such as indole, melatonin, N-[2-(5-methoxy-1H-indol-3-yl)ethyl]acetamide, skatole and indole-3-carbinol; certain bioflavenoids such as quercetin methyl chalcone, and anti-inflammatory fatty acids such as TES TRIOLATE, or PX-13 have also demonstrated utility in the treatment of hair loss and accordingly these compounds may be added to the composition of the invention.

Anti-fungal materials have also demonstrated utility in the treatment of hair loss. Accordingly, the composition may comprise an anti-fungal material. Suitable antifungal materials include azole antifungal agents such as ketoconazole, miconazole, clotrimazole, econazole, bifonazole, butoconazole, fenticonazole, isoconazole, oxiconazole, sertaconazole, sulconazole, tioconazole, fluconazole, itraconazole, isavuconazole, ravuconazole, posaconazole, voriconazole and terconazolepolyene; polyene antifungal agents such as natamycin, rimocidin, filipin, nystatin, amphotericin B and candicin; allylamines such as terbinafine, amorolfine, naftifine and butenafine; echinocandin antifungal agents such as anidulafungin, caspofungin and micafungin, and other known antifungal agents such as benzoic acid in combination with a keratolytic agent, ciclopirox, flucytosine, griseofulvin, gentian violet haloprogintolnaftate, undecylenic acid and tea tree oil. The azole antifungal agents are of particular utility since they also inhibit the synthesis of testosterone, which function can also be useful in the treatment or prevention of hair loss conditions and disorders as described above.

Anti-inflammatory agents are effective at reducing inflammation and pain and may have a secondary effect on hair loss disorders. Anti-inflammatory agents suitable for use in the composition of the invention include, but are not limited to 2-Arylpropionic acids (profens), salicylates, arylalkanoic acids, N-Arylanthranilic acids (fenamic acids), pyrazolidine derivatives, oxicams, COX-2 inhibitors, sulphonanilides and other known anti-inflammatory agents such as licofelone and omega-3 fatty acids. Most preferably ibuprofen is comprised as the anti-inflammatory agent.

Antipruritic agents or constituents which provide a mild analgesic may be added to the composition to reduce associated side effects such as irritation or itching. Such compositions include, but are not limited to zinc oxide (calamine), methol, phenol and camphor.

The cardiac glycoside may be comprised in the composition in a sequestered form, i.e. the composition may comprise a molecule which is capable of forming an inclusion compound with the cardiac glycoside to control delivery of the active ingredient. For example, the composition may comprise a cyclodextrin.

Preferably, the composition is suitable for topical administration to a patient. The compositions contemplated by this invention include compositions adopted for topical application to the human scalp and/or skin. Conventional composition forms for this purpose include ointments, lotions, pastes, jellies, gels, mousses, sprays, foams, aerosols, powders and similar known composition forms.

Therefore, the composition may also comprise a suitable carrier or diluent. Suitable carriers or diluents may be aqueous and/or alcoholic and may include a viscous base to retain the composition in situ in use. Suitable diluents for use as carriers to form a lotion include water and lower alcohols or polyols, such as methanol, ethanol, isopropanol, glycerol or propylene glycol. To form a cream or ointment a paraffinic fraction and an emulsion base may be used. The carrier may also comprise other conventional carriers or diluents, such as, for example, glucose, lactose, corn starch, starch paste, gum acacia, gelatin, mannitol, magnesium trisilicate, potato starch, urea, keratin or colloidal silica.

The term "ointment" includes creams having oleaginous water soluble emulsion bases, for example lanolin, petrolatum, glycols, glycerin and similar.

The compounds may be liposomal preparations or liquid emulsions or dissolved in conventional solvents such as acetonitrile, dimethylformamide (DMF), dimethylacetamide (DMA), alcohols such as propanol and similar.

Optionally, the composition may be adapted for oral administration to a patient. Conventional composition forms for this purpose include tablets, coated tablets, caplets, troches, lozenges, dispersions, suspensions and capsules and similar known composition forms.

Alternatively, the composition may be adapted for parenteral administration. Conventional routes of parental administration include intravenous, intramuscular, intralesional, intraarterial, subcutaneous, intradermal, transdermal, transmucosal and inhalational and similar known routes. Preferably, the composition is administered by intramuscular or intralesional routes.

The composition may further comprise at least one component selected from the group consisting of a mineral supplement, a vitamin supplement, essential oils, fragrances, colouring agents, preservatives and a skin absorption enhancer.

Suitable mineral supplements for use in the composition include, but are not limited to, iron, zinc, copper, magnesium and calcium and combinations thereof.

Suitable vitamin supplements for use in the composition include, but are not limited to, vitamin A (retinol), B group vitamins such as vitamin B1 (thiamine), vitamin B2 (riboflavin), vitamin B3 (niacin), vitamin B5 (pantothenic acid), vitamin B6 (pyridoxine pyridoxal or pyridoxamine), B7 (Biotin), B9 (folic acid) and B12 (cobalamin), vitamin C (ascorbic acid), vitamin D (calciferol), vitamin E (tocopherol) and vitamin K (phyllochinone) and combinations thereof.

Suitable essential oils for use in the composition include, but are not limited to jasmine oil, tea tree oil and citrus oils.

Suitable fragrances for use in the composition include menthol, benzyl alcohol, eugenol, phenoxyethanol, isopropyl palmitate, isopropyl myristate, benzyl salicylate, phenylethyl salicylate, thymol, isoamyl salicylate, triton X-100 surfactant, benzoic acid, benzyl benzoate, methyl salicylate, phenol, oleic acid, caproic acid or carbaryl.

Conventional colouring agents suitable for use in the composition include, but are not limited to, tartrazine, quinoline yellow, sunset yellow, amaranth, ponceau 4R, erythrosine, red 2G, allura red AC, patent blue V, indigo carmine, brilliant blue FCF, fast green FCF, green S and iron oxides.

Suitable preservatives for use in the composition include, but are not limited to, parabens such as methyl and propyl paraben, sorbic acid, potassium sorbate, quaternium-15, methylchloroisothiazolinone, and Iodopropynyl butylcarbamate (IPBC) and natural preservatives such as citrus oils.

The composition may additionally comprise a skin absorption enhancer to facilitate absorption of the composition through the skin of the patient. Suitable skin absorption enhancers for this purpose include pentane 1,5-diol, N-dodecyl-2-pyrrolidone and its acetate analogue, fatty acids such as oleic acid, terpenes, esters such as isopropyl myristate, khellin and khellin analogues, methyl nicotinate, MSM-decylmethylsulfoxide, diethylene glycol, citric acid, pyruvic acid, phenoxyethanol, transcutol, phosphatidyl choline, a medium chain triglyceride oil (MCT oil) and water.

Administration of the composition to the affected area of a patient may be carried out in any manner which will result in delivery of an effective amount of the composition to the affected area of the patient. Preferably, the composition is applied topically to the affected area of the patient, which may be the scalp or another body surface. Preferably, the composition is administered topically to the affected area or areas between one and three times daily, and most preferably twice daily. Optionally, the composition in the form of a shampoo may be used daily for treatment of the condition either alone, or in combination with the topical administration.

The frequency of the application as well as the application time may be varied according to the individual objective. For example, the hair loss composition may be applied as a shampoo which is immediately rinsed out or may be applied as a lotion, shampoo, ointment or gel which is applied to the affected area and left to penetrate into the skin for a period of time. The ointment formulations are particularly suitable for use on facial areas such as the eyebrows or beard, whereas the spray formulations are preferred for diffuse types of hair loss such as male or female pattern hair loss or telogen effluvium. Gel and lotion formulations are suitable for all types of hair loss. Liposome formulations may be used for all types of hair loss, but are particularly suitable in cases where the patient is devoid of any existing hair, for example severe cases of alopecia areata, alopecia totalis and alopecia universalis.

In each case, it is recommended that the hair treatment composition is used on a regular basis and for a period of time to meet the specified objective of prevention of hair loss and/or stimulation of regrowth.

The invention will now be described by way of illustration only in the following examples:

Example 1

A composition in accordance with the invention for administration as a lotion or a spray was prepared as follows:

| | |
|---|---|
| Digoxin | 0.025% w/w |
| Ibuprofen | 2% w/w |
| Alcohol | 30% w/w |
| Propylene Glycol | 10% w/w |
| Glycerine | 5% w/w |
| Purified Water | to 100% |

Example 2

A composition in accordance with the invention for administration as a lotion or a spray was prepared as follows:

| | |
|---|---|
| Digipuratum standardized extract | 2.2% w/w |
| Ibuprofen | 5% w/w |
| Alcohol | 30% w/w |
| Propylene Glycol | 10% w/w |
| Glycerine | 5% w/w |
| Polysorbate | 1% w/w |
| Purified Water | to 100% |

Example 3

A composition in accordance with the invention for administration as a lotion or a spray was prepared as follows:

| | |
|---|---|
| Fluid Extract of *Digitalis* (5% w/v) | 5% w/w |
| Ethanol 95° | 25% w/w |
| Preservative | 0.3% w/w |
| Fragrance | 0.05% w/w |
| Oil of birch tar | 5% w/w |
| Polysorbate 80 | 1% w/w |
| Citric acid 10% | qs |
| Deionised water | to 100% |

A sufficient quantity of citric acid (where qs denotes "Quantum Sufficiat") was employed to adjust the pH of the composition to pH 5.5.

Example 4

A base composition for administration as a spray formula was prepared with purified water, aloe vera gel, hydrolysed soy protein, glycerin, propylene glycol, polysorbate-20, allantoin, (B Complex), Panthenol, B5, B6, B12, diazolinydinyl urea, methylparaben, propylparaben, oligosaccharides, polysaccharides, and fragrance. The active ingredient of the cardiac glycoside digoxin was added to the composition in an amount of 0.04% w/v to prepare a hair loss composition in accordance with the invention. The above composition can also be prepared using proscillaridin-A as the active ingredient.

Example 5

A base composition in accordance with the invention for administration as a cooling lotion (anti-pruritic) or a spray was prepared as follows:

| | |
|---|---|
| Menthol | 75 gm |
| Salicylic acid | 75 gm |
| Talcum | 7.5 kg |
| Zinc Oxide | 7.5 kg |
| Glycerin | 5 L |
| Alcohol | 20 L |
| Water | 20 L |

The cardiac glycoside active ingredient digoxin (0.04% w/v) was added to the base composition in order to prepare a hair loss composition in accordance with the invention.

Example 6

A oil-in-water emulsion composition in accordance with the invention was prepared as follows:

| | |
|---|---|
| Digoxin | 0.025% w/w |
| Ibuprofen | 3% w/w |
| Cyclodextrin | 2% w/w |
| Emulsifying wax | 9% w/w |
| White soft paraffin | 15% w/w |
| Liquid paraffin | 6% w/w |
| Phenoxyethanol | 1% w/w |
| Deionised water | to 100% |

Example 7

A composition in accordance with the invention for administration as a cooling lotion was prepared as follows:

| | |
|---|---|
| Digoxin | 0.04% w/w |
| Calamine | 15% w/w |
| Zinc Oxide | 5% w/w |
| Bentonite | 3% w/w |
| Sodium Citrate | 0.5% w/w |
| Liq. Phenol | 0.5% w/w |
| Glycerin | 5% w/w |
| Purified Water | to 100% |

Example 8

A composition in accordance with the invention for administration as a lotion or a spray was prepared as follows:

| | |
|---|---|
| Cardiac glycoside (Digipuratum) | 1.4% w/v |
| Ibuprofen | 2% w/w |
| Alcohol | 30% w/w |
| Propylene Glycol | 10% w/w |
| Glycerine | 5% w/w |
| Polysorbate | 1% w/w |
| Purified Water | To 100% |

Example 9

A composition in accordance with the invention for administration as a shampoo was prepared with a fluid extract of *digitalis* in an amount of 2% w/v in combination with deionised water, sodium laureth sulfate, cocamidopropylbetaine, cocamide DEA, sodium lauryl sulfate, glycolstearate, wheat oligosaccharides, hydrolyzed wheat protein, silk amino acids, cocodimonium hydroxypropyl hydrolyzed hair keratin, panthenol, hair keratin amino acids, hydroxypropyl methylcellulose, extracts of aloe, sarsaparilla, senna, sheep sorrel, hops extract and birch, polysorbate 20, octyl methoxycinnamate, DMDM hydantoin, iodopropynyl butylcarbamate, citric acid, fragrance and tetrasodium EDTA.

Example 10

A composition in accordance with the invention for administration as a shampoo was prepared with an infusion of *digitalis* in an amount of 2% w/v in combination with deionised water, sodium laureth sulfate, cocamidopropylbetaine, cocamide DEA, sodium lauryl sulfate, glycolstearate, wheat oligosaccharides, hydrolyzed wheat protein, silk amino acids, cocodimonium hydroxypropyl hydrolyzed hair keratin, panthenol, hair keratin amino acids, hydroxypropyl methylcellulose, extracts of aloe, sarsaparilla, senna, sheep sorrel, hops extract, birch and white ginger, polysorbate 20, octyl methoxycinnamate, DMDM hydantoin, iodopropynyl butylcarbamate, citric acid, fragrance and tetrasodium EDTA.

Example 11

An emulsifying ointment in accordance with the invention was prepared as follows:

| | |
|---|---|
| Cardiac glycoside (Digipuratum) | 2.75% w/v |
| Cardiac glycoside (Digoxin) | 0.025% w/w |
| Salicylic acid | 2% w/w |
| White soft paraffin | 46% w/w |
| Liquid paraffin | 20% w/w |
| Emulsifying wax | to 100% |

Example 12

An emulsifying ointment in accordance with the invention was prepared as follows:

| | |
|---|---|
| Cardiac glycoside (Digoxin) | 0.04% w/w |
| Phospholipids | 2% w/w |
| Zinc oxide | 15% w/w |
| Calcium hydroxide | 0.045% w/w |
| Oleic acid | 0.5% w/w |
| Almond oil | 32% w/w |
| Wool fat | 8% w/w |
| Purified Water | to 100% |

Case Study 1—Trichotillomania

The composition of example 1 was applied as a lotion twice daily to the scalp of a 19 year old woman suffering from trichotillomania. In the patient under study, the repeated self-plucking of the scalp hair had resulted in a condition known as trichomalacia, in which the affected hair follicles are plugged and contain soft, deformed, swollen hairs.

Within 10-12 weeks of treatment being commenced, fine downy hair called "vellus" was observed to be growing on the scalp. The twice daily topical application was continued until the regrowth was well established all over the scalp region. Most notably, hair regrowth was established also in areas of the scalp to which the lotion had not been applied but which bordered with the areas of application of the composition.

Case Study 2—Female Pattern Hair Loss

The spray composition of example 3 was used in combination with the shampoo composition of example 10 to treat a 39 year old Caucasian female suffering from female pattern hair loss Ludwig scale II. Thinning of the hair was apparent at the top and centre of the scalp. Previous treatment with known hair loss compositions had resulted in deleterious side-effects with severe rashes appearing on the face and the scalp.

At the early stages of pattern baldness hair follicles become miniaturized and produce small vellus hairs. These miniaturized hair follicles can potentially be reactivated however to produce full terminal hairs.

The composition of example 3 was applied directly as a spray twice daily to the afflicted area with the composition of example 10 being used daily as a shampoo. The compositions were well tolerated by the patient with no apparent signs of allergic reaction and no irritation reported.

A reduction in hair loss was noted after ten weeks of treatment. Regrowth was noted after twenty-four weeks of treatment with the rejuvenation of the existing miniaturized hairs and the rest of the scalp hairs looking much healthier with increased hair density. The regrowth pattern was slow and steady.

Case Study 3—Traumatic Alopecia

The composition of example 1 in the form of a lotion was applied daily to the scalp of a 38 year old female with Negroid hair. The female presented with traumatic alopecia resulting from hairstyling, and in particular, extensive use of hair straighteners. Affected areas of between 5 and 10 cm were prominently visible along the frontal lines of the hair. The composition was applied twice a day continuously for a period of 12 months.

Initial signs of regrowth were observed at between 14-18 weeks after commencement of the daily treatment. The regrowth achieved was slow, but continuous.

Case Study 4—Androgenetic Alopecia

The spray composition of example 3 was applied three times daily to the scalp of a 34 year old male presenting with androgenetic alopecia with Norwood/Hamilton grades III-IV with thinning apparent at the top and centre of the scalp. In addition, the shampoo of example 9 was used daily. The compositions were well tolerated by the patient with no signs of irritation even with the high levels of application. Treatment was continued for 12 months with initial non-pigmented vellus hair regrowth being observed after 16 weeks and significant improvement in hair density and regrowth apparent at the 12 month stage.

Case Study 5—Alopecia Areata (65% Severity)

The composition of example 1 was used to treat a female of approximately 45 years of age suffering from a severe case of alopecia areata (65% severity). The alopecia had presented initially in the patient as a single circumscribed and totally bald, smooth patch on the scalp with further patches of hair loss soon apparent. Within six months the bald patches were numerous and continued to expand in size and number. Prescribed pharmaceutical compositions failed to alter the progression of the condition and after three years the alopecia areata was steadily progressing towards alopecia totalis with up to 75% hair loss noted on the scalp areas and signs of alopecia visible on the eyebrows.

The cardiac glycoside composition of example 1 was applied topically as a lotion to the affected areas three times a day. The compositions were well tolerated by the patient with no signs of irritation or reaction even with the high levels of application Treatment was continued for 32 weeks. Two new patches of alopecia developed in the patient on the fourth week of treatment, but initial non-pigmented vellus hair regrowth was observed after nine weeks of treatment. Full regrowth on the eyebrows was achieved at approximately 26 weeks with a 100% scalp hair regrowth being obtained at the end of the treatment period.

Case Study 6—Alopecia Areata (90% Severity)

The lotion composition of example 1 was used to treat a 52 year old female with a severe case of alopecia areata (90% severity). Two years after the initial onset of the condition, the alopecia areata was steadily progressing to alopecia totalis with severity on the scalp areas at around 95% and signs of alopecia patches apparent on both eyebrows. Facial, body and pubic hair was also noticeably scarce.

The cardiac glycoside composition was applied topically as a lotion to the affected areas twice a day and the shampoo of example 10 was used daily. Treatment was continued for a period of 60 weeks, with a break from application of the lotion after 40 weeks lasting for two weeks. The compositions were well tolerated by the patient with no signs of irritation or reaction even with the continued high levels of application Initial regrowth was observed on the ninth week of treatment with non-pigmented vellus hair growth observed. Facial, body and pubic hair were the first to show signs of regrowth. Progress halted at approximately 24 weeks and application of the lotion was increased to three times daily. After approximately 4 weeks at the higher level of application hair growth appeared to accelerate and the application was continued until 60 weeks by which time a complete scalp hair growth had been achieved.

Case Study 7—Alopecia Barbae

The emulsifying ointment composition of example 12 was used to treat a 27 year old Caucasian man presenting with alopecia barbae. The subject had developed two symmetrical patches of hair loss of approximately 4×4 cm on the beard area. The moustache areas of the patient were not affected. The composition was applied topically to the affected area 2-3 times a day and full recovery of the alopecia patches was achieved after 16 weeks of continuous treatment.

Case Study 8—Alopecia Areata and Alopecia Barbae

The compositions of examples 1 and 12 were used to treat a 44 year old Caucasian man with alopecia areata and alopecia barbae. The patient presented with five patches on the scalp ranging from 8×5 cm to 3×3 cm in circumference. The patient also had two patches of hair loss on the beard, each patch measuring approximately 5×4 cm and signs of alopecia on the moustache.

The compositions were each applied twice daily. The emulsifying ointment composition of example 12 was applied to the affected areas of the beard, whilst the lotion of example 1 was applied to the affected area of the scalp. After approximately 7-8 weeks, initial regrowth in the form of new vellus hairs was observed on the beard area with full regrowth on the beard and moustache area being achieved after 16 weeks. Complete regrowth on the scalp areas was achieved after 28 weeks of continuous daily treatment.

Case Study 9—Alopecia Areata

The compositions of examples 1 and 9 were used to treat a 45 year old Caucasian woman with alopecia areata which had rapidly progressed to alopecia universalis within the course of a year, with body hair noticeably absent. Previous prescribed medications had failed to halt the progress of the condition.

The cardiac glycoside composition of example 1 was applied as a lotion to the scalp and eyebrow areas of the patient three times a day with the shampoo composition of example 9 being employed to cleanse the scalp once a day.

Initial signs of hair regrowth were observed within three months of commencement of the facial and body hair the first to show signs of regrowth. Thereafter tiny non-pigmented vellus-type hairs being observed on the scalp, which eventually grew into terminal-type hairs after a short vellus cycle.

The subject continued with the topical applications until a complete scalp hair regrowth was achieved after approximately 18 months, with a break from using the composition for two weeks at 30 and 60 weeks respectively.

The lotion and shampoo formulation were well tolerated by the patient with no signs of allergic reaction or skin irritation noted.

Case Study 10—Monilethrix

The cardiac glycoside compositions of examples 8 and 10 were used in the treatment of monilethrix in an 18 year old Caucasian female. The patient exhibited the classic signs of monilethrix with diffuse hair loss and the remaining weakened hair fibres having the appearance of a string of beads. Monilethrix is a rare disorder, most commonly inherited as an autosomal dominant trait, which is characterized by sparse, dry and/or brittle hair that often breaks before reaching more than a few inches in length. The hair may lack lustre and there may be patchy areas of hair loss. Another common symptom may be the appearance of elevated spots (papules) surrounding the hair follicles that may be covered with brown crusts or scales (perifollicular hyperkeratosis). When viewed under a microscope, the hair shaft resembles a string of evenly spaced beads. In monilethrix, hair loss is most frequently observed at the back of the scalp and neck with the front of the head often relatively unaffected. In this case the patient noted that periodically she would exhibit spontaneous partial regrowth of the hair which would subsequently fall out. Previously prescribed medications had failed to halt hair loss or achieve significant regrowth.

The cardiac glycoside lotion composition of example 8 was applied topically to the scalp and eyebrow areas two times a day, while the shampoo of example 10 was used to cleanse the hair every second day.

Initial regrowth was observed on the twelfth week of treatment with the growth of tiny non-pigmented vellus hair. Treatment was continued until full regrowth was achieved after a period of 34 weeks. Twelve months after the treatment ceased, the newly regrown hair had not fallen off.

The overall condition and appearance of the scalp hair that was characterized by sparse, dry and/or brittle hair that often broke before reaching more than a few inches in length was greatly improved and the overall scalp hair quality, length and density was greatly improved.

It is apparent that the compositions comprising cardiac glycosides are effective in the treatment of hair loss resulting from a variety of conditions and disorders. Whilst the mode of action of the cardiac glycoside compositions described herein is not fully understood, it is believed that cardiac glycosides may have a positive effect on hair regrowth by increasing the flow of blood to the affected hair follicles. However, the inventor has observed that even after the cessation of treatment with the above compositions, hair growth was maintained in many cases, unlike conventional treatments which function by increasing blood flow. Furthermore, as noted in case study 1, regrowth was established in areas to which the composition had not been directly applied. Thus, it is believed that the subject cardiac glycosides may have a secondary immunomodulatory effect which can act systemically to restore normal immune function, possibly by inhibiting binding of a natural substrate to a receptor or an enzyme involved in an inflammatory process.

The invention claimed is:

1. A composition for the treatment of hair loss, said composition consisting of: extract of *Digitalis*, ethanol, birth tar oil, polysorbate 80, citric acid, water, a preservative, and a fragrance.

2. The composition as claimed in claim 1, wherein said preservative is selected from the group consisting of methyl paraben, propyl paraben, sorbic acid, potassium sorbate, quaternium-15, methylchloroisothiazolinone, Iodopropynyl butylcarbamate (IPBC), and citrus oils.

3. The composition as claimed in claim 1, wherein said fragrance is selected from the group consisting of menthol, benzyl alcohol, eugenol, phenoxyethanol, isopropyl palmitate, isopropyl myristate, benzyl salicylate, phenylethyl salicylate, thymol, isoamyl salicylate, benzoic acid, benzyl benzoate, methyl salicylate, phenol, oleic acid, and caproic acid.

4. The composition as claimed in claim 1, wherein said extract of *Digitalis* is present in an amount of 5% by weight.

5. A composition for the treatment of hair loss, said composition consisting of: digoxin, ibuprofen, cyclodextrin, an emulsifying wax, at least one paraffin, phenoxyethanol, and water.

6. The composition as claimed in claim 5, wherein said paraffin is white soft paraffin, and liquid paraffin.

7. The composition as claimed in claim 5, wherein said digoxin is present in an amount of 0.025% by weight.

8. A composition for the treatment of hair loss, said composition consisting of: a digoxin, calamine, zinc oxide, bentonite, sodium citrate, liquid phenol, glycerin, and water.

9. The composition as claimed in claim 8, wherein said digoxin is present in an amount of 0.04% by weight.

10. A composition for the treatment of hair loss, said composition consisting of: digipuratum, digoxin, salicylic acid, at least one paraffin, and an emulsifying wax.

11. The composition as claimed in claim 10, wherein said paraffin is white soft paraffin, and liquid paraffin.

12. The composition as claimed in claim 10, wherein said digipuratum is present in an amount of 2.75% by weight, and said digoxin is present in an amount of 0.025% by weight.

13. A composition for the treatment of hair loss, said composition consisting of: digoxin, phospholipids, zinc oxide, calcium hydroxide, oleic acid, almond oil, wool fat, and water.

14. The composition as claimed in claim 13, wherein said digoxin is present in an amount of 0.04% by weight.

15. A composition for the treatment of hair loss, said composition consisting of: a digoxin, ibuprofen, propylene glycol, glycerine, water, and an alcohol selected from the group consisting of menthol, ethanol, and isopropanol.

16. A composition for the treatment of hair loss, said composition consisting of: a digoxin, menthol, salicylic acid, talcum, zinc oxide, glycerin, water, and an alcohol selected from the group consisting of ethanol, and isopropanol.

17. A method of treating hair loss by applying to the hair a composition according to claim 1.

18. A method of treating hair loss by applying to the hair a composition according to claim 5.

19. A method of treating hair loss by applying to the hair a composition according to claim 8.

20. A method of treating hair loss by applying to the hair a composition according to claim 10.

21. A method of treating hair loss by applying to the hair a composition according to claim 13.

22. A method of treating hair loss by applying to the hair a composition according to claim 15.

23. A method of treating hair loss by applying to the hair a composition according to claim 16.

* * * * *